United States Patent [19]

Tanaka et al.

[11] Patent Number: 5,470,827

[45] Date of Patent: Nov. 28, 1995

[54] METHOD OF PRODUCING ITURIN A AND ANTIFUNGAL AGENT FOR PROFOUND MYCOSIS

[75] Inventors: Yasushi Tanaka, Chiba; Takashi Tojo; Kazuhiko Uchida, both of Choshi; Jun Uno, Tokyo; Yasushi Uchida, Saga; Osamu Shida, Choshi, all of Japan

[73] Assignee: Higeta Shoyu Co., Ltd., Tokyo, Japan

[21] Appl. No.: 312,911

[22] Filed: Sep. 29, 1994

[30] Foreign Application Priority Data

Sep. 30, 1993 [JP] Japan .................................. 5-265446
Sep. 20, 1994 [JP] Japan .................................. 6-250150

[51] Int. Cl.$^6$ .......................... C12P 21/04; A61K 38/12
[52] U.S. Cl. ........................... 514/11; 435/71.2; 435/71.3; 435/167; 530/317; 530/321
[58] Field of Search .................................. 530/317, 321; 514/11; 435/71.2, 71.3

[56] References Cited

U.S. PATENT DOCUMENTS 5,061,495  10/1991  Rossall .................................. 435/71.3

FOREIGN PATENT DOCUMENTS

| 4205196 | 9/1992 | Germany . |
| 202416 | 12/1984 | Japan . |
| 2-240004 | 9/1990 | Japan . |
| 5-085911 | 4/1993 | Japan . |
| 6-135811 | 5/1994 | Japan . |

OTHER PUBLICATIONS

Chem Abs: 121:294975 Klich et al. "Mycopatologia" (1994) 127(2) 123–127.
Chem Abs. 121:276511 Jacques et al. "Proceedings 6th Eur. Cong. Biotech" 1993 Pt. 2 pp. 1067–1070.
Hatada; *Plant Pathogenic Germ Sporulation Inhibitor*, Patent Abstracts of Japan, The Patent Office Japanese Government, vol. 11, No. 159; May 22, 1987.
Hatada; *Production of Factor For Suppressing Sporulation of Phytopathogenic Fungus*, Patent Abstracts of Japan, The Patent Office Japanese Government, vol. 11, No. 159; May 22, 1987.
Isoagi et al; *Structures of B–Amino Acids in Antibiotics Iturin A*, Tetrahedron Letters, vol. 23, No. 30, pp. 3065–3068; 1982.
Nippon Byori Gakkai Kaishi, *Opportunistic Fungus Infection*, Tr. Soc. Pathol. Jpn., vol. 74, pp. 61–91, 1985.
Medoff et al, *Antifungal Agents Useful in Therapy of Systemic Fungal Infections*, Ann. Rev. Pharmacol. Toxicol., vol. 23, pp. 303–330, 1983.
Isogai et al, *Structures of B–Amino Acids in Antibiotics Iturin A*, Tetrahedron Letters, vol. 23, No. 30, pp. 3065–3068, 1982.
Delcambe et al, *L'Iturine, Nouvel Antibiotique Produit Par Un Bacillus Subtilis*, C. R. Soc. Biol., vol. 144, pp. 1431–1434, 24, Jun. 1950
Clairbois et al, *D'Essais Cliniques Et Biologiques Sur L'Iturine, Antifunique Nouveau*, Arch. Belges. Derm. Et. Syph., vol. 14, pp. 63–82, 1985.

*Primary Examiner*—Herbert J. Lilling
*Attorney, Agent, or Firm*—Browdy and Neimark

[57] ABSTRACT

The present invention is a method of producing iturin A, in which cells of *Bacillus amyloliquefaciens* are incubated and iturin A is collected from the culture. It also relates to an antifungal agent for profound mycosis, containing iturin A as the active ingredient. Heretofore, there have been known few medicines effective against profound mycosis, but iturin A may be an effective antifungal agent for profound mycosis.

1 Claim, 2 Drawing Sheets

FIG. 2

METHOD OF PRODUCING ITURIN A AND ANTIFUNGAL AGENT FOR PROFOUND MYCOSIS

DETAILED EXPLANATION OF THE INVENTION

1. Industrial Field of the Invention

The present invention relates to a method of producing iturin A and to an antifungal agent for profound mycosis comprising iturin A as the active ingredient.

2. Prior Art

Heretofore, infectious diseases to be caused by fungi such as mold, yeast and others have been essentially in local infection in the skin, respiratory organs, vagina and others, but recently, these tend to increase also in systemic infection. In particular, systemic infectious diseases such as profound infectious diseases to be caused by depression of immunological competence resulting from use of immunosuppressive agents, carcinostatics and others are increasing. Many cases of fatal serious infectious diseases have been reported in the clinical medicine (Nippon Byori Gakkai Kaishi, 74, 61 (1985)). However, as compared with noticeable progress of the chemotherapy for infectious diseases to be caused by bacteria, it must be said that the chemotherapy for infectious diseases to be caused by fungi is belated at present. One reason is that bacteria are prokaryocytes, being different from animal cells of eukaryocytes with respect to the cell background, and preparation of medicines having selective toxicity to them is easy; while fungi which are composed of eukaryocytes like animal cells are hardly differentiated from animal cells because of the similar cell background of them so that elevation of the selective toxicity specific only to fungi but not to animal cells is not easy.

At present, only amphotericin B is known as a medicine effectively applicable to profound mycosis such as candidiasis, aspergillosis, cryptococcosis, mucormycosis, coccidioidomycosis, paracoccidioidomycosis, blastomycosis, histoplasmasis, sporotrichosis, etc. (Annu. Rev. Pharmacol., Toxicol., 23, 303 (1983)).

PROBLEMS TO BE SOLVED BY THE INVENTION

The object of the present invention is to provide a method of producing known iturin A and to provide an antifungal agent for profound mycosis which comprises iturin A as the active ingredient and which is useful as a medicine for preventing and curing profound, fungal infectious diseases.

MEANS FOR SOLVING THE PROBLEMS

The present inventors broadly searched natural substances, especially microbial metabolites for antifungal substances and, as a result, have found that certain bacteria belonging to the genus Bacillus produce a substance which is effective against fungi in their cultures. They examined the microbiological properties of the strain, which was identified to be *Bacillus amyloliquefaciens*. This was deposited in the National Institute of Bioscience and Human-Technology, Agency of Industrial Science and Technology in Japan, as *Bacillus amyloliquefaciens* HSCC 124 (FERM BP-4758).

The following Table 1 shows the microbiological properties of *Bacillus amyloliquefaciens* HSCC 124.

TABLE 1

Microbiological Properties of *Bacillus amyloliquefaciens* HSCC 124

(A) Morphological Properties (in broth-agar medium):

| | |
|---|---|
| (1) Cell Size: | $3\mu$ to $5\mu \times 0.5\mu$ to $0.9\mu$ |
| (2) Cell Shape: | bacillus form |
| (3) Polymorphism of Cell: | Negative |
| (4) Motility: | Positive (as peritrichous flagella) |
| (5) Sporulation: | Positive |
| (6) Gram Stain: | Positive after incubation for 12 to 48 hours |

(B) Growth in Media:

| | |
|---|---|
| (1) Broth-agar Plate Culture: | The cells grew well to form circular, flat yellowish-gray colonies, having endogenous gloss. |
| (2) Broth-agar Slant Culture: | The cells grew well to form spread cloth-like, yellowish-gray colonies, having endogenous gloss. |
| (3) Broth Liquid Culture: | The culture became slightly cloudy. The cells grew on the surface of the liquid culture to form film-like colonies. Precipitate formed in the culture was infinitesimal. |
| (4) Decomposition of Gelatin: | + |
| (5) Litmus Milk: | The grown cells reduced litmus and decomposed milk. |

(C) Physiological Properties:

| | |
|---|---|
| (1) Reduction of Nitrates: | – |
| (2) MR Test: | – |
| (3) V-P Test (pH 5.5): | + |
| (4) Formation of Indole: | – |
| (5) Hydrolysis of Starch: | + |
| (6) Utilization of Citric Acid, | |
| Koser: | + |
| Christensen: | + |
| (7) Utilization of Inorganic Nitrogen Sources, | |
| $NO_3$: | – |
| $NH_4$: | + |
| (8) Formation of Dye: | – |
| (9) Urease: | – |
| (10) Oxidase: | + |
| (11) Catalase: | + |
| (12) Range for Growth: | |
| pH for Growth: | 5 to 9 |
| Optimum Temperature: | 30° C. |
| (13) Influence by Oxygen: | aerobic |

(14) Formation of Acid and Gas from Saccharides:

| | Acid | Gas |
|---|---|---|
| L-arabinose | +/– | – |
| D-xylose | + | – |
| D-glucose | + | – |

TABLE 1-continued

Microbiological Properties of *Bacillus amyloliquefaciens* HSCC 124

| | | |
|---|---|---|
| D-mannose | + | – |
| D-fructose | +/– | – |
| D-galactose | – | – |
| Maltose | +/– | – |
| Sucrose | + | – |
| Lactose | +/– | – |
| Trehalose | + | – |
| D-sorbitol | + | – |
| D-mannitol | + | – |
| Inositol | – | – |
| Glycerin | +/– | – |
| Starch | + | – |
| (15) NaCl Tolerance: | | |
| NaCl 5%: | | + |
| NaCl 7%: | | + |
| (D) Chemotaxonomical Properties: | | |
| (1) Base Composition of DNA (GC content): | 46.4 mol % | |
| (2) DNA-DNA Homology with *B. amyloliquefaciens* DSM 7: | 81% | |

Based on these findings, the present inventors further searched various strains of *Bacillus amyloliquefaciens* stored in the microorganisms-storing organ for those producing antifungal substances and found that the cells of *Bacillus amyloliquefaciens* IAM 1523 also produce the same antifungal substance in their culture. They isolated the antifungal substance from the cultures of *Bacillus amyloliquefaciens* HSCC 124 and *Bacillus amyloliquefaciens* IAM 1523 and identified its structure. As a result, they found that the substance was the same as iturin A that had been identified to be a mixture comprising 8 peptide compounds (Tetrahedron Lett., 23, 3065–3068 (1982)). Iturin A is a substance that was found and identified by L. Delcambe et al. (C. R. Soc. Biol., 144, 1431–1434 (1950)), and there are known some examples demonstrating the production of iturin A by *Bacillus subtilis*. However, there is known no example demonstrating the production of the same by *Bacillus amyloliquefaciens*, and it is unknown that *Bacillus amyloliquefaciens* may produce iturin A. Specifically, the present invention relates to a method of producing iturin A by incubating *Bacillus amyloliquefaciens* and collecting iturin A from its culture.

It is known that iturin A has an antifungal activity against various fungi (ARCH. BELGES. DERM. ET. SYPH., 14, 63–82 (1958)). The present inventors investigated the effectiveness of iturin A against fungi to cause profound mycosis which has been considered problematic in these days and have found that iturin A is effective against profound mycosis. Heretofore, there has been known no report suggesting the effectiveness of iturin A against profound mycosis. The present inventors are the first who have completed the antifungal agent for profound mycosis, comprising iturin A as the active ingredient, on the basis of the effectiveness of iturin A against profound mycosis.

Accordingly, the present invention is a method of producing iturin A by incubating *Bacillus amyloliquefaciens* and collecting iturin A from its culture. In addition, it is also an antifungal agent for profound mycosis, comprising iturin A as the active ingredient. The active ingredient to be in the antifungal agent for profound mycosis of the present invention may be any of iturin A, preferably including iturin A2 to iturin A8.

According to the method of the present invention for producing iturin A, any of strains of iturin A-producing *Bacillus amyloliquefaciens*, their variants or mutants is inoculated in a nutrient medium containing carbon sources and nitrogen sources and incubated therein under aerobic conditions (for example, by shaking culture, aerial stirring culture, etc.) whereby iturin A is produced in the culture.

Any of carbon sources that may be assimilated by iturin A-producing microbes may be employed in the present invention. Preferred are glucose, sucrose, starch, fructose, glycerin and other carbohydrates.

Like carbon sources, any of nitrogen sources that may be assimilated by iturin A-producing microbes may be employed in the present invention. Preferred are oat meal, yeast extract, peptone, gluten meal, cotton seed meal, soybean meal, corn steep liquor, dry yeast, wheat germ, peanut meal, chicken bone meal and others. Also advantageously usable are inorganic and organic nitrogen compounds, for example, ammonium salts (such as ammonium nitrate, ammonium sulfate, ammonium phosphate and others), urea, amino acids and others. Use of combinations of such carbon sources and nitrogen sources is advantageous, but it is not always necessary to use only pure ones. This is because impure ones often contain growth factors or micro nutrients.

If desired, inorganic salts such as those mentioned below may be added to the medium. They are, for example, sodium carbonate, potassium carbonate, sodium phosphate, potassium phosphate, sodium chloride, potassium chloride, sodium iodide, potassium iodide, magnesium salts, copper salts, cobalt salts and others.

In particular, where the medium is a strongly foaming one, liquid paraffin, animal oils, vegetable oils, mineral oils, silicones, higher alcohols and the like may be added thereto, if desired.

For industrial mass-production of the intended product, the microorganisms are preferably incubated by aerial stirring culture like the case of producing other fermentation products. Where a small amount of the intended product is produced, they are preferably incubated by shaking culture in a flask.

Where the incubation is effected in a large-size tank, it is preferred that the iturin A-producing microorganisms are first inoculated and cultivated in a relatively small amount of a medium and thereafter the resulting culture is transferred to a large-size production tank in which the previously grown microorganisms are further incubated to produce the intended product, for the purpose of preventing their delay in growing and producing iturin A. In this case, the composition of the medium to be used in the preculture and that of the medium to be used for the latter incubation to produce the intended product, iturin A may be the same one, or if desired, they may be different from each other.

The incubation is preferably effected under the condition of aerial stirring. For example, any known method, such as stirring culture with propellers or other mechanical stirrers, rotary or shaking culture in a fermenter, pumping or air-blowing culture or the like, may suitably be employed. Air to be used for aeration of the culture system is desired to be previously sterilized.

The incubation temperature may suitably be varied within the range where the iturin A-producing microorganisms may produce the present substance, iturin A. In general, the incubation may be effected at 10° to 40° C., preferably 25° to 35° C. The incubation time varies, depending on the incubation condition and the amount for fermentation, and it is generally approximately from one day to one week.

After completion of the fermentation, the culture obtained is recovered as iturin A, which is the active ingredient to be in the antifungal agent for profound mycosis of the present invention. The iturin A to be in the antifungal agent for profound mycosis of the present invention is purified by known methods to a pure one that is acceptable as a medicine. To obtain a pure product from the culture, for example, when iturin A is in the cells in the culture, the cells are directly extracted with water and/or organic solvent(s) or, alternatively, these are disrupted mechanically or ultrasonically or by any other known means and thereafter extracted with water and/or organic solvent(s). Then, the product is recovered and purified by ordinary methods. When iturin A is in the culture, the culture may directly be extracted with solvent(s) or, alternatively, it may be filtered through a filter membrane or the like. If desired, the culture may be brought into contact with an active charcoal, powdery cellulose, adsorbing resin or the like carrier so that the produced iturin A is adsorbed to the carrier, and thereafter the product may be desorbed therefrom by elution.

For further purifying the product, any ordinary recovering and purifying method for harvesting antibiotics may be employed. For instance, usable are solvent extraction with water, organic solvents or mixed solvents of them; chromatography; recrystallization from a single solvent or a mixed solvent; and other ordinary means. These may be employed singly or in combination of them.

Iturin A which is to be in the antifungal agent for profound mycosis of the present invention, as the active ingredient, may be produced by the above-mentioned microorganisms, and it may be a purified one. Apart from this, however, iturin A produced by any other iturin A-producing microbes as well as iturin A chemically synthesized may also be employed in the present invention.

To use iturin A as an antifungal agent for profound mycosis according to the present invention, iturin A may be used as it is or, alternatively, it may be blended with a pharmaceutically-acceptable, non-toxic and inert carrier to form a drug composition containing, for example, from 0.1% to 99.5%, preferably from 0.5% to 90% of iturin A. Iturin A or the drug composition containing iturin A is administered to animals including human beings.

As the carrier, usable are one or more solid, semi-solid or liquid diluting agents, fillers and other ordinary drug additives. The drug composition is desired to be administered as its dose unit. The drug composition of the present invention may be administered by oral administration, tissue administration, local administration (such as endermic administration, etc.) or rectal administration. It may also be used for external application. Needless to say, the drug composition is administered as a form suitable to the administration route.

It is desired that the amount of the antifungal agent of the present invention to be actually used is adjusted in consideration of the condition of the patient, such as its age or body weight, the administration route, the condition and degree of the disease and others. In general, the amount to be administered to one adult is from 10 to 2000 mg a day, as the active ingredient of the present invention. As the case may be, the necessary amount may be smaller than the range or may be larger than the same. If a large amount of the medicine is administered, it is desired that the total amount thereof a day is divided into several parts for separate administration in one day.

Oral administration of the medicine may be effected, using its solid or liquid dose unit of, for example, powder, powder mixture, tablets, dragées, capsules, drops, sublingual tablets and other preparation forms.

Powder of the medicine may be produced by grinding the active substance into a desired fineness. Powder mixture of it may be produced by grinding the active substance into a desired fineness followed by blending the resulting powder with a fine powdery drug carrier, such as a fine powdery edible carbohydrate of, for example, starch, mannitol or the like. If desired, a flavoring, a preservative, a dispersing agent, a colorant, a perfume and other additives may be added to the preparation.

Capsules of the medicine may be produced by encapsulating powder, powder mixture or granules of the medicine with a capsule coat such as a gelatin capsule coat. Prior to the encapsulation, a lubricant or fluidizing agent, such as colloidal silica, talc, magnesium stearate, calcium stearate, solid polyethylene glycol or the like powdery substance may be incorporated into the powdery or granular medicine. Addition of a disintegrator or a solubilizer, for example, carboxymethyl cellulose, calcium carboxymethyl cellulose, hydroxypropyl cellulose of low substitution degree, calcium carbonate or sodium carbonate, to the medicine preparation to be encapsulated is recommended so as to elevate the effectiveness of the medicine when the capsules have been ingested.

If desired, the fine powdery medicine of the present invention may be suspended and dispersed in a vegetable oil along With polyethylene glycol, glycerin and a surfactant and the resulting dispersion may be wrapped with a gelatin sheet to give soft capsules.

Tablets of the medicine may be produced by granulating or slagging the active substance-containing powder mixture followed by adding a disintegrator or lubricant thereto and forming the resulting blend into tablets.

The powder mixture comprises a suitably powdered active substance and the above-mentioned diluting agent and base and/or may optionally contain a binder (for example, sodium carboxymethyl cellulose, alginates, gelatin, polyvinyl pyrrolidone, polyvinyl alcohol, etc), a slow-releasing agent (for example, paraffin, etc.), a reabsorbing agent (for example, quaternary salts) and/or an adsorbent (for example, bentonite, kaolin, dicalcium phosphate, etc.). The powder mixture may be wetted with a binder such as syrup, starch paste, gum arabic, cellulose solution or polymer substance solution and then forcedly sieved to give granules. In place of forming granules from the powder in this manner, the powder may directly be processed with a tabletting machine and thereafter the resulting slugs of an incomplete form may be pulverized to granules.

A lubricant such as stearic acid, stearates, talc, mineral oils and others may be added to the granules to be obtained in this manner, so as to prevent their adhesion to each other. The lubricant-containing mixture is then formed into tablets. If desired, the active substance may directly be formed into tablets, after having been combined with a fluid inactive carrier, without taking the above-mentioned granulating or slagging step. As the case may be, a transparent or semi-transparent protective film composed of a shellac sealant film, or a sugar or polymer material film, or a waxy lubricant top coat film may be employed for overcoating the tablets.

Other oral preparations, such as solution, syrup, elixir and the like may also be produced in the unit dose form of containing a determined amount of the active substance. Syrup may be produced by dissolving the active compound in a suitable aromatizing aqueous solution; and elixir may be produced by blending it with a non-toxic alcoholic carrier. Suspension may be formulated by dispersing the active compound in a non-toxic carrier. A solubilizer and an emulsifier (for example, ethoxylated isostearyl alcohols, polyoxyethylene sorbitol esters), a preservative, an aromatizing agent (such as peppermint oil, saccharin) and others may optionally be added to them.

If desired, the unit dose formulation for peroral administration may be encapsulated into microcapsules. The formulation may be coated with a coating film or may be embedded into polymer substances, wax or the like so as to prolong the active life of the active substance or to attain slow release of the active substance.

Parenteral administration may be effected, using a liquid dose unit form of, for example, a solution or suspension for subcutaneous, intramuscular or intravenous injection. This may be prepared by dissolving or suspending a determined amount of the active compound in a non-toxic liquid carrier suitable for injection of, for example, an aqueous or oily medium followed by sterilizing the resulting solution or suspension. Alternatively, a determined amount of the active compound may be put in a vial and thereafter the vial may be sterilized along with the content and then sealed. For dissolution or mixing of the powdery or freeze-dried active compound just before its administration, a preparatory vial or carrier may be prepared along with it. For making the injection containing the active compound isotonic, a non-toxic salt or salt solution may be added thereto. If desired, a stabilizer, a preservative, an emulsifier and the like may also be added thereto.

Rectal administration may be effected, using a suppository composed of the active compound and a low melting point solid of, for example, polyethylene glycol, cacao butter, higher esters (e.g., myristyl palmitate) or a mixture of them.

As other preparations for parenteral administration than the above-mentioned injection and suppository, which are employable in the present invention, mentioned are intravenous drip, liquid preparation for transfusion, ointment, lotion, tonic, spray, suspension, oil, emulsion, etc. These may also be formulated by ordinary methods.

The effectiveness of the antifungal agent for profound mycosis of the present invention as a medicine may be identified by various tests.

The microbicidal spectrum of iturin A, which is the active ingredient in the antifungal agent for profound mycosis of the present invention, may be obtained, for example, from the minimum growth inhibiting concentration (MIC) of iturin A to various fungi such as clinically-isolated strains, animal-infected fungi and others to be obtained on the basis of the method as designated by Japan Chemotherapy Association.

Identification of the safety of iturin A may be effected by examining its toxicity, if any. For instance, employable for this purpose are a cytotoxicity test using animal cells and an acute toxicity test (oral single administration, intravenous single injection, intravenous repeated injection) using mice.

As one example of the test of testing the effectiveness of the active substance, iturin A, it may be administered to systemically fungi-infected mice, to which various clinically-isolated strains (*Candida albicans* IFM 40009, *Aspergillus fumigatus* Tsukuba No. 12, *Cryptococcus neoformans* 145A) were intravenously inoculated, whereby the in-vivo effectiveness of the administered substance may be examined. Of iturin A shown in Table 2 below, iturin A2 and iturin A4 were tested in said manner, and the test results obtained are shown in Tables 3 to 5 below.

TABLE 2

$$R-(CH_2)_8-\underset{NH}{CHCH_2CO} \longrightarrow L-Asn \longrightarrow D-Tyr$$

$$L-Ser \qquad\qquad\qquad D-Asn$$

$$D-Asn \longleftarrow L-Pro \longleftarrow L-Gln$$

| Name of Compound | R |
|---|---|
| A2 | $CH_3CH_2CH_2-$ |
| A3 | $CH_3CH_2CH-$<br>$\quad\;\;\mid$<br>$\quad\;\;CH_3$ |
| A4 | $(CH_3)_2CHCH_2-$ |
| A5 | $CH_3CH_2CH_2CH_2-$ |
| A6 | $(CH_3)_2CHCH_2CH_2-$ |
| A7 | $CH_3CH_2CH_2CH_2CH_2-$ |
| A8 | $CH_3CH_2CHCH_2CH_2-$<br>$\quad\quad\;\;\mid$<br>$\quad\quad\;\;CH_3$ |

TABLE 3

Number of Living Mice as Infected with *C. albicans* IFM40009

| | Test Period (day) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Control | 10 | 10 | 4 | 2 | 2 | 2 | 2 | 2 | 1 | 1 | 1 | 0 | 0 | 0 | 0 |
| Iturin A2 60 mg/kg | 10 | 10 | 5 | 5 | 5 | 5 | 3 | 3 | 3 | 2 | 1 | 1 | 0 | 0 | 0 |
| Iturin A4 60 mg/kg | 10 | 10 | 10 | 10 | 9 | 9 | 8 | 5 | 5 | 5 | 5 | 4 | 3 | 3 | 3 |

TABLE 4

Number of Living Mice as Infected with *A. fumigatus* Tsukuba No. 12

| | Test Period (day) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Control | 10 | 10 | 10 | 10 | 10 | 9 | 8 | 6 | 4 | 3 | 3 | 3 | 3 | 3 | 3 |
| Iturin A2 25 mg/kg | 10 | 10 | 10 | 10 | 10 | 10 | 9 | 7 | 5 | 4 | 4 | 3 | 3 | 3 | 3 |
| Iturin A4 25 mg/kg | 10 | 10 | 10 | 10 | 10 | 10 | 10 | 10 | 10 | 9 | 9 | 9 | 9 | 9 | 9 |

TABLE 5

Number of Living Mice as Infected with *C. neoformans* 145A

| | Test Period (day) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Control | 10 | 10 | 4 | 4 | 4 | 4 | 4 | 4 | 4 | 2 | 0 | 0 | 0 | 0 | 0 |
| Iturin A2 10 mg/kg | 10 | 10 | 8 | 8 | 8 | 7 | 7 | 7 | 5 | 3 | 2 | 1 | 1 | 1 | 1 |
| Iturin A4 10 mg/kg | 10 | 10 | 6 | 5 | 5 | 5 | 5 | 5 | 5 | 5 | 3 | 1 | 0 | 0 | 0 |

From the results, it is understood that iturin A to be in the antifungal agent for profound mycosis of the present invention has a selective toxicity to fungi and strongly affects various pathogenic fungi, that its toxicity is extremely weak and that it is effective against systemic mycosis in mice. Therefore, it has strongly been suggested that the antifungal agent for profound mycosis of the present invention is effective as a remedy for various fungi-infected diseases such as candidiasis, aspergillosis, cryptococcosis, etc.

Next, the present invention will be explained in more detail by means of the following examples, which, however, are illustrative ones and are not intended to restrict the scope of the present invention.

EXAMPLE 1

As the seed medium, used was a medium comprising 2% of glucose, 0.5% of peptone, 0.1% of yeast extract, 0.01% of $CaCO_3$, and 0.01% of NaCl. As the production medium, used was a medium comprising 2% of fructose, 1% of peptone, 0.1% of yeast extract, 0.01% of $CaCO_3$, and 0.01% of NaCl. Both the two media were adjusted to have pH of 7.2 prior to their sterilization. 150 ml of the seed medium were put in a 500 ml-Erlenmeyer flask, which were sterilized at 120° C. for 15 minutes and then cooled. To this, inoculated were from 2 to 3 platinum loops of a slant agar culture of *Bacillus amyloliquefaciens* HSCC 124 (FERM BP-4758) and cultivated at 30° C. for 12 hours by shaking culture. Thus obtained was a seed culture of the strain. Next, 15 liters of the above-mentioned production medium were put in a 30 liter-jar fermenter, to which added were 10 ml of polypropylene glycol. This was sterilized at 120° C. for 15 minutes and then cooled. To this, inoculated were 150 ml of the above-mentioned seed culture and incubated therein at 30° C., at an aerating rate of 0.5 vvm and at a stirring rate of 150 rpm, for 12 hours. Then, 30 ml of polypropylene glycol were added thereto and the incubation was continued for further 24 hours.

Figure 1:
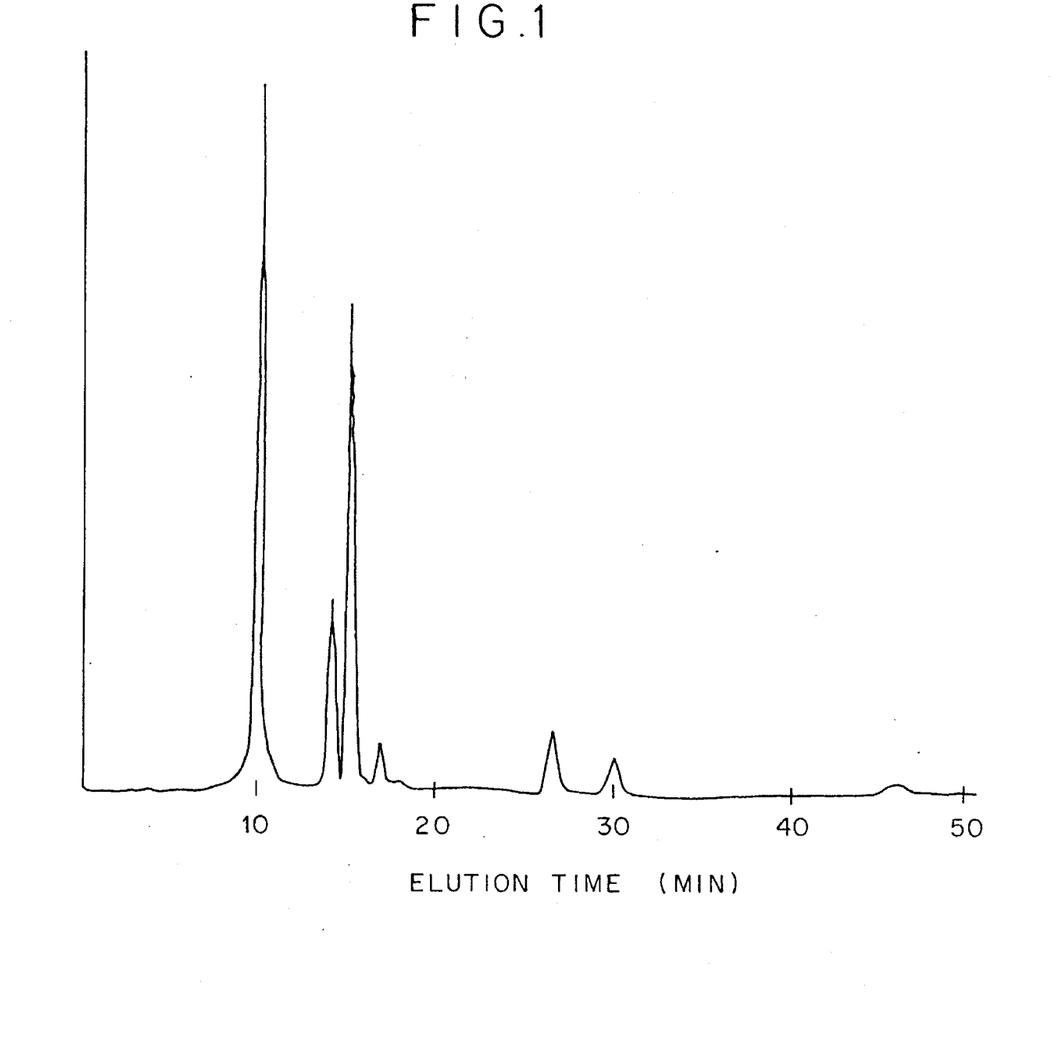
FIG. 1 shows an elution pattern of the iturin A-containing solution of Example 1.

After the incubation, 15 liters of the culture were filtered through a 0.45 μm-filter membrane, by which a mixture comprising the cells and iturin A was collected on the membrane. The mixture was then fully washed with water to remove impurities therefrom. Next, to the fraction comprising the cells and iturin A, that had remained on the membrane, added was isopropanol of from 40% to 50%, by which a fraction containing iturin A was extracted. Thus, the extract was obtained as the filtrate fraction through the 0.45 μm-filter membrane. 3 liters of the filtrate fraction were fractionated through an ultrafilter membrane having a fractionating molecular weight of 3000 to obtain a filtrate fraction passed therethrough, from which impurities were removed. Thus, 2.5 liters of an iturin A-containing liquid were obtained. The thus-fractionated, iturin A-containing fraction was passed through a column filled with 1.9 liters of ODS-C18 (made by Sohken Kagaku KK) and adsorbed to the adsorbent. The column was washed with 5 liters of 25%-acetonitrile and then eluted with 40%-acetonitrile, by which seven peaks were separated. FIG. 1 shows the elution pattern.

After having measured its biological activity, each active fraction was collected and concentrated under reduced pressure. Thus, seven fractions of iturin A were obtained, which were iturin A2 to iturin A8 shown in Table 2 above. Their yields were 300 mg, 75 mg, 120 mg, 12 mg, 40 mg, 40 mg and 10 mg, respectively.

EXAMPLE 2

Figure 2:
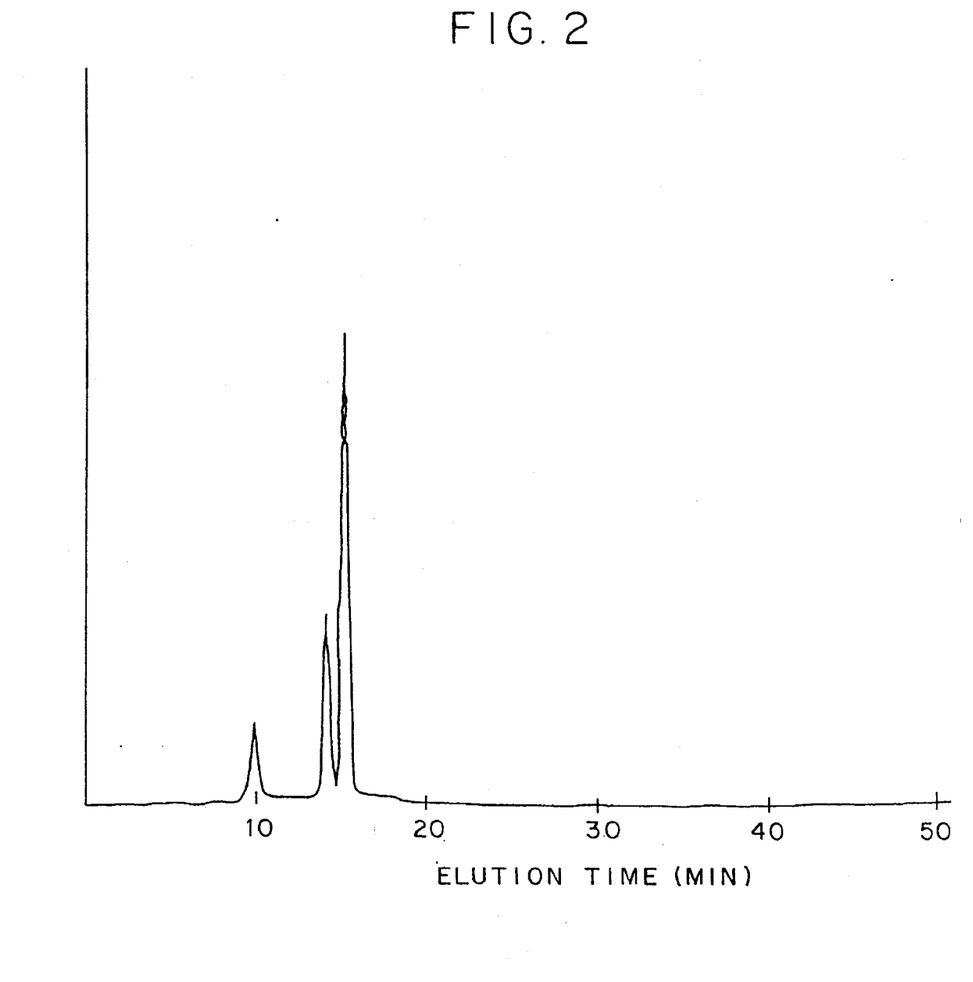
FIG. 2 shows an elution pattern of the iturin A-containing solution of Example 2.

*Bacillus amyloliquefaciens* IAM 1523 which is an iturin A-producing strain was incubated in the same manner as in Example 1. Its culture was purified also in the same manner as in Example 1 and subjected to high performance liquid chromatography to separate into three peaks. FIG. 2 shows the elution pattern. After having measured its biological activity, each active fraction was collected and concentrated under reduced pressure. Thus, three fractions of iturin A were obtained, which were iturin A2 to iturin A4 shown in Table 2 above. Their yields were 20 mg, 80 mg and 50 mg, respectively.

EXAMPLE 3

The antifungal activity of iturin A as produced in Example 1 was measured to identify its antifungal activity. Precisely, the minimum growth inhibiting concentration (MIC) of iturin A4 against fungi was measured on the basis of the method as designated by Japan Chemotherapy Association, and the results shown in Table 6 below were obtained. From these results, it has been verified that iturin A is strongly effective against various pathogenic fungi.

In addition, MIC of each of iturin A2 to iturin A8 against *Candida albicans* 7N was measured in the same manner as above, and the results shown in Table 7 below were obtained.

TABLE 6

Antifungal Activity of Iturin A

| Tested Fungi | | MIC (µg/ml) of Iturin A4 |
|---|---|---|
| *Candida albicans* | IFM 40001 | <0.05 |
| | IFM 40002 | 1.56 |
| | 7N | 25 |
| *C. krusei* | IFM 40019 | 25 |
| *C. tropicalis* | IFM 40018 | 6.25 |
| *C. glabrata* | IFM 40065 | 6.25 |
| *Cryptococcus neoformans* | IFM 40038 | 3.13 |
| | IFM 40043 | 0.78 |
| *Aspergillus fumigatus* | Tsukuba No. 12 | 6.25 |
| *A. flavas* | IAM 2044 | 2.4 |
| *Mucor guilliermondii* | IFO 9403 | 1.2 |

TABLE 7

Antifungal Activity (MIC) of Iturin A2 to Iturin A8 against *Candida albicans* 7N

| Compound | MIC (µg/ml) |
|---|---|
| Iturin A2 | 50 |
| Iturin A3 | 50 |
| Iturin A4 | 25 |
| Iturin A5 | 25 |
| Iturin A6 | 12.5 |
| Iturin A7 | 6.25 |
| Iturin A8 | 12.5 |

Fungi used: *Candida albicans* 7N
Medium used: 0.5% Glucose, Yeast-nitrogen base (made by DIFCO Co.)

EXAMPLE 4

Iturin A as produced in Example 1 was tested with respect to its toxicity, by which its safety was verified.
(1) Cytotoxicity Test:

A floating suspension of CHL/IU cells, having a concentration of $1.3 \times 10^5$ cells/ml, was prepared, and this was separately put in a 96-well micro-plate in an amount of 100 µl/well. The cells were incubated at 37° C. for 48 hours, and the medium was exchanged for 180 µl/well of a fresh medium. Then, iturin A4 (obtained in Example 1) having a concentration of 10 mg/100 µl was diluted to 1/10 with the medium to have a maximum concentration. The diluted one having a maximum concentration was further stepwise diluted to ½, ¼ . . . at regular intervals in four stages. 20 µl of the dilution having a varying concentration was added to each well and the cells therein were incubated for further 48 hours at 37° C. After 48 hours, MTT/PBS solution having a concentration of 5 mg/ml was diluted to ½ and 20 µl of the dilution was added to each well. After reacted for 4 hours, the plate was subjected to centrifugation at 1000 rpm for 5 minutes, 200 µl of the supernatant was removed, and 100 µl of 10% Triton X-100 containing 0.04N HCl/isopropanol was added to the residue. The amount of MTT formazan as eluted was measured with a microplate reader (by Corona Co.; MTP-120) (main wavelength 570 nm; side wavelength 630 nm).

Evaluation of the toxicity was effected in the manner mentioned below. Briefly, the average of the absorbance of the control well (Ac) and the average of the absorbance of the test well to which a varying concentration of iturin A4 had been added (At) were obtained, and drug-sensitivity of [At/Ac]×100 was obtained therefrom for evaluation of the toxicity. The value is a criterion of the viability of the tested cells. The results obtained are shown in Table 8 below. As is understood from the results, iturin A4 had no cytotoxicity to the incubated animal cells in a concentration of from 1 to 0.5 mg/ml or less and therefore the extremely high safety of iturin A4 was verified.

TABLE 8

| | Cytotoxicity Test | | | | | |
|---|---|---|---|---|---|---|
| Amount of Active Substance Added to Each Well (mg/ml) | 1.0 | 0.5 | 0.25 | 0.125 | 0.06125 | Control |
| Average Absorbance | 0.005 | 0.036 | 0.411 | 0.429 | 0.446 | 0.428 |
| [At/Ac] × 100 (%) | 1.2 | 8.4 | 96.0 | 100.2 | 104.2 | — |

(2) Acute Toxicity Test:

Iturin A4 obtained in Example 1 was dissolved in an injectable distilled water to prepare an aqueous 10% (w/v) solution of iturin A4 to be tested. The test solution was forcedly oral-administered once to five male and five female ddy-N mice, after having been fasted for 13 hours, by the use of a stomach probe. The test ddy-N mice were about 4-week age ones and were obtained from Nippon Medico-Chemical Animal Sources Laboratories Co., Ltd. Prior to the test, all the test mice were preliminarily bred in the laboratory for one week so as to confirm the healthy condition of them. Then, the about 5-week age mice were subjected to the test. The body weight of the test mice just before the test was 28 g (male mice) and from 18 to 22 g (female mice).

To each of the male and female mice, the test solution was administered in an amount of 20 ml per kg of the body weight, whereby 2,000 mg/kg of the test substance was administered to them. Just after the administration, the vitality of all the test mice lowered slightly, but it came back to be normal in 2 hours after the administration. One hour after recovery of the vitality of them, they were fed, and the time-dependent mortality of the test mice was observed for 2 weeks. The results obtained are shown in Table 9 below.

TABLE 9

Acute Toxicity Test

| Sex | Amount Administered (mg/kg) | Time-Dependent Mortality 1 | 2 3 4 5 6 ... 14 days | Mortality (%) | $LD_{50}$ (mg/kg) |
|---|---|---|---|---|---|
| Male Mice | 2,000 | 0/5 | ... 0/50 | 0 | >2,000 |
| Female Mice | 2,000 | 0/5 | ... 0/50 | 0 | >2,000 |

In the next test, mice of the same kind as mentioned above were used. Iturin A4 was dissolved in DMSO(dimethylsulfoxide)-castor oil-5% Glc solution, and the resulting solution was injected to the caudal vein of each of the five male mice once or plural times. For the single injection, the solution was administered to the mice each in an amount of 200 mg per kg of the body weight; and for the plural injections, it was administered to them 14 times each in an amount of 30 mg/kg/day. After the injection(s), the time-dependent mortality of the test mice was observed and the results shown in Tables 10 and 11 below were obtained.

TABLE 10

Time-Dependent Mortality of Test Mice by Single Intravenous Injection

| Sex | Amount Administered (mg/kg) | Time-Dependent Mortality 1 | 2 3 4 5 6 ... 14 days | Mortality (%) | $LD_{50}$ (mg/kg) |
|---|---|---|---|---|---|
| Male Mice | 200 | 0/5 | ... 0/50 | 0 | >200 |

TABLE 11

Time-Dependent Mortality of Test Mice by Plural Intravenous Injections

| Sex | Amount Administered (mg/kg/ day × times) | Time-Dependent Mortality 1 | 2 3 4 5 6 ... 14 days | Mortality (%) |
|---|---|---|---|---|
| Male Mice | 30 × 14 | 0/5 | ... 0/5 | 0 |

As is obvious from the above-mentioned results, oral administration of iturin A resulted in no death of the test mice, and the anatomical view of the test mice gave no abnormality. In the animal tests, $LD_{50}$ of the test substance, iturin A as calculated by a probit method was more than 2000 mg/kg. The guide line by OECD (Apr. 11, 1986) and others have defined that the maximum peroral dose of a chemical substance to a mouse in the acute toxicity test is 2000 mg/kg, from which the low toxicity of iturin A has been verified. $LD_{50}$ of iturin A by single intravenous injection and that by plural intravenous injections were both more than 200 mg/kg or more, from which the low toxicity and the safety of iturin A in injection have been verified like the case of its oral administration.

EXAMPLE 5

50 mg of iturin A7 were dissolved in 4 ml of DMSO. Apart from this, 42 mg of cholesterol were dissolved in 4 ml of methanol under heat, to which 16 ml of hot 10% HCO-60 (made by Nippon Surfactant Co.) were added to prepare a cholesterol solution. After cooled, the cholesterol solution was added to the previously-prepared iturin A7 solution, to which 16 ml of water were added. The resulting solution was transferred into a vial and freeze-dried to prepare an iturin A7 preparation.

This was dissolved in 40 ml of 5% glucose solution, which was mixed with 500 ml of 5% glucose solution to prepare a preparation for dripping.

EXAMPLE 6

40 ml of 5% glucose solution were added to each of 10 vials containing the iturin A7 preparation produced in Example 1 to dissolve the preparation. These were mixed together and blended with 140 ml of 5% glucose solution to prepare a solution for oral administration.

EXAMPLE 7

Tablets were formed from (1) 50 g of iturin A4, (2) 90 g of lactose, (3) 29 g of corn starch and (4) 1 g of magnesium stearate. Precisely, (1) and (2) were mixed along with (3) (17 g), and the mixture was granulated along with a paste prepared from (3) (7 g). (3) (5 g) and (4) were added to the resulting granules and well blended, and the resulting blend was tabletted with a compression tabletting machine to produce 1000 tablets containing 50 mg/tablet of the active ingredient (1).

ADVANTAGE OF THE INVENTION

The present invention provides an antifungal agent for profound mycosis comprising, as the active ingredient, iturin A. Iturin A is extremely effective in preventing and curing human and animal profound mycosis caused by fungi. It can be administered to animals including human beings by oral administration, external application, endermic application, intravenous injection or other administration routes.

We claim:

1. A process for the treatment of profound mycosis, comprising administering to an animal in need of such treatment, an amount of iturin A sufficient for the treatment of said profound mycosis.

* * * * *